US008507207B2

(12) United States Patent
Cheng et al.

(10) Patent No.: US 8,507,207 B2
(45) Date of Patent: Aug. 13, 2013

(54) RECOMBINANT NUCLEOTIDE SEQUENCE, CELL OR VECTOR CONTAINING THE SAME AND METHOD FOR USING CELL CONTAINING THE SAME TO ENCODE ANTI-POLYETHYLENE GLYCOL MONOCLONAL ANTIBODIES

(75) Inventors: Tian-Lu Cheng, Kaohsiung (TW); Steve R. Roffler, Taipei (TW); Kuo-Hsiang Chuang, Chiayi (TW)

(73) Assignee: Kaohsiung Medical University, Kaohsiung (TW)

(*) Notice: Subject to any disclaimer, the term of this patent is extended or adjusted under 35 U.S.C. 154(b) by 468 days.

(21) Appl. No.: 12/766,930

(22) Filed: Apr. 26, 2010

(65) Prior Publication Data

US 2011/0064651 A1 Mar. 17, 2011

(30) Foreign Application Priority Data

Sep. 17, 2009 (TW) ............................... 98131334 A

(51) Int. Cl.

| | |
|---|---|
| *G01N 33/53* | (2006.01) |
| *C12Q 1/68* | (2006.01) |
| *C12N 15/64* | (2006.01) |
| *C12N 15/00* | (2006.01) |
| *C07H 21/04* | (2006.01) |

(52) U.S. Cl.

USPC ........... 435/7.1; 435/6.1; 435/6.19; 435/91.4; 435/320.1; 536/23.53

(58) Field of Classification Search

None

See application file for complete search history.

(56) References Cited

U.S. PATENT DOCUMENTS

2008/0057519 A1* 3/2008 McWhirter .................. 435/7.23

* cited by examiner

*Primary Examiner* — Anne Gussow
*Assistant Examiner* — Channing S Mahatan
(74) *Attorney, Agent, or Firm* — Pai Patent & Trademark Law Firm; Chao-Chang David Pai

(57) ABSTRACT

The invention provides a recombinant nucleotide sequence, including the sequence of SEQ ID No. 1, SEQ ID No. 2, SEQ ID No. 3 or SEQ ID No. 4, wherein the recombinant nucleotide sequence encodes an anti-polyethylene glycol recombinant single chain membrane antibody.

5 Claims, 13 Drawing Sheets

PEG-NIR 797

RECOMBINANT NUCLEOTIDE SEQUENCE, CELL OR VECTOR CONTAINING THE SAME AND METHOD FOR USING CELL CONTAINING THE SAME TO ENCODE ANTI-POLYETHYLENE GLYCOL MONOCLONAL ANTIBODIES

CROSS REFERENCE TO RELATED APPLICATIONS

This Application claims priority of Taiwan Patent Application No. 098131334, filed on Sep. 17, 2009, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0911-A21209-US_Seq_Listing.txt"; its date of creation is Feb. 2, 2010; and its size is 24,505 bytes.

BACKGROUND OF THE INVENTION

1. Field of the Invention

The present invention relates to a novel reporter gene system, and in particular relates to a method for using a recombinant nucleotide sequence encoding an anti-polyethylene glycol recombinant single chain membrane antibody as a reporter gene to monitor presence and distribution of a gene and a cell.

2. Description of the Related Art

Developing non-immunogic and specific reporter genes to monitor expressions and distributions of genes and cells in vivo is very important for the optimization of gene or cell therapy.

Presently, there are two types of reporter genes for non-invasive imaging: (1) exogenous reporter genes: mainly from bacterium or virus of non-mammal systems, such as the gene of the herpesvirus thymidine kinase, the gene of the bacterial cytosine deaminase and the gene of the green fluorescent protein. Although exogenous reporter genes have specificities, the products thereof usually induce immune responses that result in tissue injury. Thus, exogenous reporter genes limit the continuous expression (long term) and orientation imaging of reporter genes, limiting clinical application; and (2) endogenous reporter genes: from such as human dopamine D2 and transferrin. Although endogenous reporter genes do not easily induce immune responses, dopamine D2 and transferrin are widely expressed in normal human body systems. Thus, endogenous reporter genes lack specificity and application thereof is limited. Therefore, developing low immunogic and highly specific reporter genes is desired. As such, a gene of an anti-polyethylene glycol membrane antibody which belongs to the exogenous reporter genes and meets the low immunogenicity and high specificity features and requirements of reporter genes is disclosed herein.

BRIEF SUMMARY OF THE INVENTION

The invention provides a recombinant nucleotide sequence, comprising the sequence of SEQ ID No. 1, SEQ ID No. 2, SEQ ID No. 3 or SEQ ID No. 4, wherein the recombinant nucleotide sequence encodes an anti-polyethylene glycol recombinant single chain membrane antibody.

The invention also provides a vector comprising the recombinant nucleotide sequence of the invention.

The invention also provides a cell comprising the recombinant nucleotide sequence of the invention.

The invention provides another cell comprising the vector of the invention.

The invention further provides an anti-polyethylene glycol recombinant single chain membrane antibody, comprising: a first part, comprising a variable light chain-kappa constant (VL-CK) region, and an amino acid sequence thereof comprising the sequence of SEQ ID No. 5 or SEQ ID No. 6; and a second part, comprising a variable heavy chain-heavy chain first constant (VH-CH1) region, and an amino acid sequence thereof comprising the sequence of SEQ ID No. 7 or SEQ ID No. 8, wherein the first part and the second part is connected by a disulfide bond.

The invention further provides a method for using a cell, comprising: (a) providing a living being having the cell claimed in claim 6, wherein the cell expresses the anti-polyethylene glycol recombinant single chain membrane antibody on a cell membrane thereof; (b) injecting a polyethylene glycol imaging probe into the living being, wherein the polyethylene glycol imaging probe binds to the anti-polyethylene glycol recombinant single chain membrane antibody, and the polyethylene glycol imaging probe is formed by a polyethylene glycol connecting to an imaging agent; and (c) using an imaging system to observe a region presenting the anti-polyethylene glycol recombinant single chain membrane antibody in the living being.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
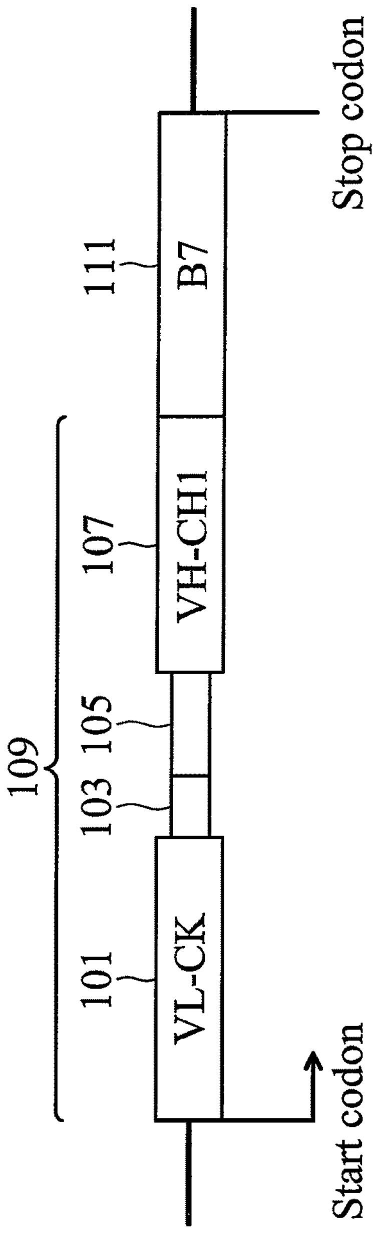
FIG. 1 shows a construction illustration for a recombinant nucleotide sequence, the sequence of SEQ ID No. 1, of the invention.

FIG. 1 shows a construction illustration for a recombinant nucleotide sequence, the sequence of SEQ ID No. 1, of the invention. First, polymerase chain reactions (PCRs) are performed using total RNA of a hybridoma secreting anti-polyethylene glycol monoclonal antibody as a template and a universal primer pair which is able to obtain a gene sequence of a variable light chain-kappa constant (VL-CK) region for all antibodies of mice and using total RNA of a hybridoma secreting anti-polyethylene glycol monoclonal antibody as a template and a universal primer pair which is able to obtain a gene sequence of a variable heavy chain-heavy chain first constant (VH-CH1) region for all antibodies of mice, respectively, to obtain a gene sequence of a variable light chain-kappa constant (VL-CK) region of the hybridoma secreting anti-polyethylene glycol monoclonal antibodies (the sequence of SEQ ID No. 9) 101 and a gene sequence of a variable heavy chain-heavy chain first constant (VH-CH1) region of the hybridoma secreting anti-polyethylene glycol monoclonal antibodies (the sequence of SEQ ID No. 12) 107, respectively.

A nucleotide sequence encoding furin-cleavage site 103 is the sequence of SEQ ID. No. 10 and a nucleotide sequence encoding foot and mouth disease virus 2A processing sequence 105 is the sequence of SEQ ID. No. 11.

Then, 101-105, the sequences of SEQ ID Nos. 9-12 are fused in order to form 109, the sequence of SEQ ID No. 13 by a method, such as a polymerase chain reaction method.

Next, a nucleotide sequence encoding a transmembrane region of B7 protein (the sequence of SEQ ID No. 14) 111 is fused to a 3' end of the sequence of SEQ ID No. 13 to form a recombinant nucleotide sequence of the invention, the sequence of SEQ ID. No. 1, which may encode an anti-polyethylene glycol recombinant single chain membrane antibody.

In another embodiment, a nucleotide sequence encoding hemagglutinin (HA) (the sequence of SEQ ID No. 15) is fused to a 5' end of the sequence of SEQ ID No. 1 to form the sequence of SEQ ID No. 2 which may also encode an anti-polyethylene glycol recombinant single chain membrane antibody.

In further another embodiment, first a nucleotide sequence encoding myc protein (the sequence of SEQ ID No. 16) is fused to a 3' end of the sequence of SEQ ID No. 1 and then a nucleotide sequence encoding a transmembrane region of B7 protein (the sequence of SEQ ID No. 14) is fused to a 3' end of the sequence of SEQ ID No. 16 which has been connected to the sequence of SEQ ID No. 1 to form the sequence of SEQ ID No. 3 which may also encode an anti-polyethylene glycol recombinant single chain membrane antibody.

Moreover, a nucleotide sequence encoding hemagglutinin (HA) (the sequence of SEQ ID No. 15) may be fused to a 5' end of the sequence of SEQ ID No. 3 to form the sequence of SEQ ID No. 4 which may also encode an anti-polyethylene glycol recombinant single chain membrane antibody.

The recombinant nucleotide sequence of the invention may be used as a reporter gene by fusing with a promoter of a gene that needs to be monitored. Specifically, a polyethylene glycol imaging probe may specifically bind to an anti-polyethylene glycol recombinant single chain membrane antibody, so that gene expressions and distributions of the gene that needs to be monitored may be observed. The anti-polyethylene glycol recombinant single chain membrane antibody encoded by the recombinant nucleotide sequence may be expressed on a cell membrane of a cell. In one embodiment, the cell mentioned above may comprise a stem cell, tumor cell or immune cell. A cell or a vector may comprise the recombinant nucleotide sequence of the invention or a cell may comprise a vector containing the recombinant nucleotide sequence of the invention. The cell may comprise a stem cell, tumor cell or immune cell and the vector may comprise a plasmid, viral vector or non-viral vector.

Figure 2:
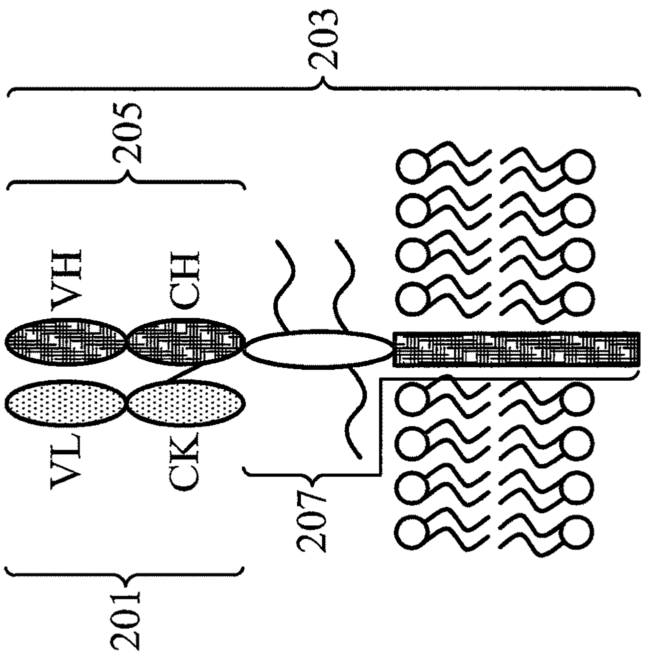
FIG. 2 shows a structure illustration for an anti-polyethylene glycol recombinant single chain membrane antibody encoded by the recombinant nucleotide sequence of the invention.

After the recombinant nucleotide sequence of the invention is translated by a cell, the 2A processing sequence encoded from the recombinant nucleotide sequence of the invention is cleaved to separate a light chain amino sequence of the anti-polyethylene glycol recombinant single chain membrane antibody from a heavy chain amino sequence of the anti-polyethylene glycol recombinant single chain membrane antibody. Following, the separated light chain and heavy chain amino sequences of the membrane antibody of the invention is assembled as the membrane antibody in an endoplasmic reticulum (ER). Furthermore, since the furin cleavage site is between the light chain sequence of the antibody and 2A processing sequence, after the membrane antibody enters a Golgi apparatus, the remaining 2A processing sequence after the light chain sequence is completely cleaved by a Furin protease to express a functional membrane antibody on a cell membrane of a cell. In one embodiment, the cell mentioned above may comprise a stem cell, tumor cell or immune cell. FIG. 2 shows a structure illustration for an anti-polyethylene glycol recombinant single chain membrane antibody encoded by the recombinant nucleotide sequence of the invention. The anti-polyethylene glycol recombinant single chain membrane antibody may comprise a first part 201 comprising a variable light chain-kappa constant (VL-CK) region, and a second part 203 comprising a variable heavy chain-heavy chain first constant (VH-CH1) region 205 and a transmembrane region 207, wherein the first part 201 and the second part 203 is connected by a disulfide bond.

In one embodiment, the anti-polyethylene glycol recombinant single chain membrane antibody is encoded by the sequence of SEQ ID No. 1, and thus an amino sequence of the first part thereof is the sequence of SEQ ID No. 5 and an amino sequence of the second part thereof is the sequence of SEQ ID No. 7.

In another embodiment, the anti-polyethylene glycol recombinant single chain membrane antibody is encoded by the sequence of SEQ ID No. 2, and thus an amino sequence of the first part thereof is the sequence of SEQ ID No. 6 and an amino sequence of the second part thereof is the sequence of SEQ ID No. 7.

In another embodiment, the anti-polyethylene glycol recombinant single chain membrane antibody is encoded by the sequence of SEQ ID No. 3, and thus an amino sequence of the first part thereof is the sequence of SEQ ID No. 5 and an amino sequence of the second part thereof is the sequence of SEQ ID No. 8.

In further another embodiment, the anti-polyethylene glycol recombinant single chain membrane antibody may be encoded by the sequence of SEQ ID No. 4 and thus an amino sequence of the first part thereof is the sequence of SEQ ID No. 6 and an amino sequence of the second part thereof is the sequence of SEQ ID No. 8.

In addition, a method for using a cell containing the recombinant nucleotide sequence of the invention may comprise providing a living being having the cell of the invention, wherein the cell expresses the anti-polyethylene glycol recombinant single chain membrane antibody on the cell membrane thereof. After that, a polyethylene glycol imaging probe is injected into the living being and the polyethylene glycol imaging probe will specifically bind to the anti-polyethylene glycol recombinant single chain membrane antibody, wherein the polyethylene glycol imaging probe is formed by a polyethylene glycol connecting to an imaging agent. Finally, an imaging system is used to observe a region presenting the anti-polyethylene glycol recombinant single chain membrane antibodies in the living being, as the polyethylene glycol imaging probe specifically binds to the anti-polyethylene glycol recombinant single chain membrane antibody.

The living being mentioned above may comprise a mammal. The cell may comprise an endogenous cell of the living being or an exogenous cell. Furthermore, the imaging agent of the invention may comprise any imaging agent able to be connected to the polyethylene glycol, such as a fluorescent imaging agent, iron oxide nanoparticle and radioactive imaging agent.

EXAMPLE

First, polymerase chain reactions (PCR) were performed using a total RNA of a hybridoma secreting anti-polyethylene glycol monoclonal antibody as a template and a primer pair (forward primer: the sequence of SEQ ID. No. 17; reverse primer: the sequence of SEQ ID. No. 18) which was able to obtain a gene sequence of a variable light chain-kappa constant (VL-CK) region for all antibodies of mice and using a total RNA of a hybridoma secreting anti-polyethylene glycol monoclonal antibody as a template and a primer pair (forward primer: the sequence of SEQ ID. No. 19; reverse primer: the sequence of SEQ ID. No. 20) which was able to obtain a gene sequence of a variable heavy chain-heavy chain first constant (VH-CH1) region for all antibodies of mice, respectively, to obtain a gene sequence of a variable light chain-kappa constant (VL-CK) region of the hybridoma secreting anti-polyethylene glycol monoclonal antibody (the sequence of SEQ ID No. 9) and a gene sequence of a variable heavy chain-heavy chain first constant (VH-CH1) region of the hybridoma secreting anti-polyethylene glycol monoclonal antibody (the sequence of SEQ ID No. 12), respectively.

Next, a polymerase chain reaction was performed by using the sequence of SEQ ID No. 9 and the sequence of SEQ ID No. 12 as a first template and a second template, respectively, the sequence of SEQ ID No. 21 (forward) and the sequence of SEQ ID No. 22 (reverse) as the primer pair for the first template, and the sequence of SEQ ID No. 23 sequence (forward) and the sequence of SEQ ID No. 24 (reverse) as the primer pair for the second template to obtain the sequence of SEQ ID No. 13. The sequence of SEQ ID No. 22 contained the entire sequence of SEQ ID No. 10, also the sequence of SEQ ID No. 23 contained the entire sequence of SEQ ID No. 11, and the sequence of SEQ ID No. 22 and the sequence of SEQ ID No. 23 had an overlapping region.

The operation condition of the polymerase chain reaction was as follows:

(1) 95° C., 2 minutes (2) 95° C., 30 seconds; 60° C., 30 seconds; 68° C., 2 minutes (for 3 cycles)

(3) 95° C., 30 seconds; 58° C., 30 seconds; 68° C., 2 minutes (for 3 cycles)

(4) 95° C., 30 seconds; 56° C., 30 seconds; 68° C., 2 minutes (for 3 cycles)

(5) 95° C., 30 seconds; 54° C., 30 seconds; 68° C., 2 minutes (for 3 cycles)

(6) 95° C., 30 seconds; 52° C., 30 seconds; 68° C., 2 minutes (for 3 cycles)

(7) 95° C., 30 seconds; 50° C., 30 seconds; 68° C., 2 minutes (for 3 cycles)

(8) 72° C., 8 minutes (9) 4° C. for storage

Figure 3:
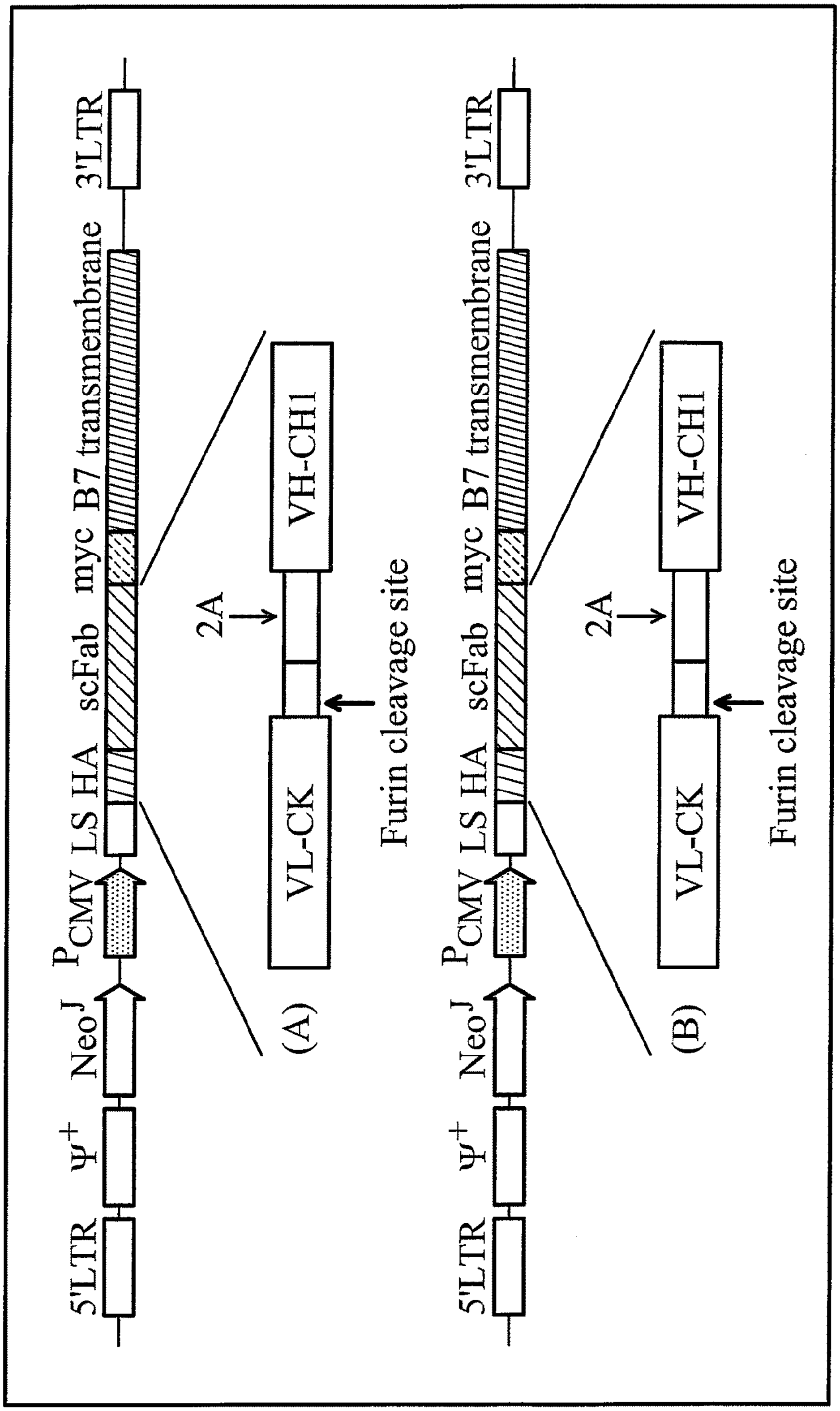
FIG. 3A shows a construction illustration for a recombinant nucleotide sequence, the sequence of SEQ ID No. 4, of the invention which encodes an anti-polyethylene glycol recombinant single chain membrane antibody.
FIG. 3B shows a construction illustration for a recombinant nucleotide sequence which encodes an anti-dansyl recombinant single chain membrane antibody.

Then, the sequence of SEQ ID No. 13 was transplanted into a retroviral vector containing the sequences of SEQ ID No. 15, SEQ ID No. 16 and SEQ ID No. 14 by utilizing designed restriction enzyme sites (Sfi 1 and Sal 1), wherein the sequence of SEQ ID No. 13 was located between the sequence of SEQ ID No. 15 and the sequence of SEQ ID No. 16, as shown in FIG. 3A.

A similar method was used to construct a nucleotide sequence encoding the anti-polyethylene glycol recombinant single chain antibody in a vector (as a control), as shown in FIG. 3B.

Determining the Light Chain and Heavy Chain of the Membrane Antibodies

Figure 4A:
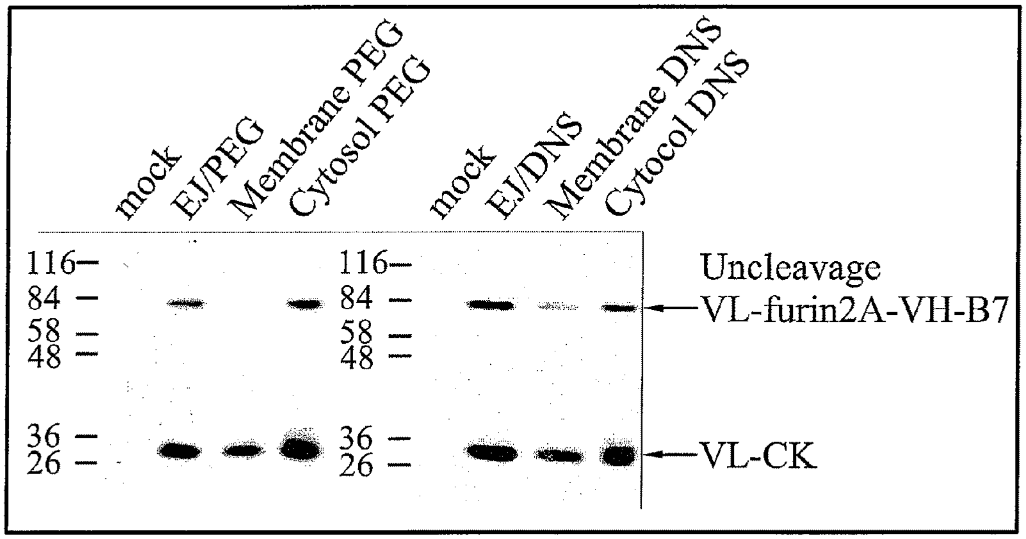
FIG. 4A shows the expression results and the molecular weights of the light chains after performing western blotting with anti-HA antigen monoclonal antibodies.
Figure 4B:
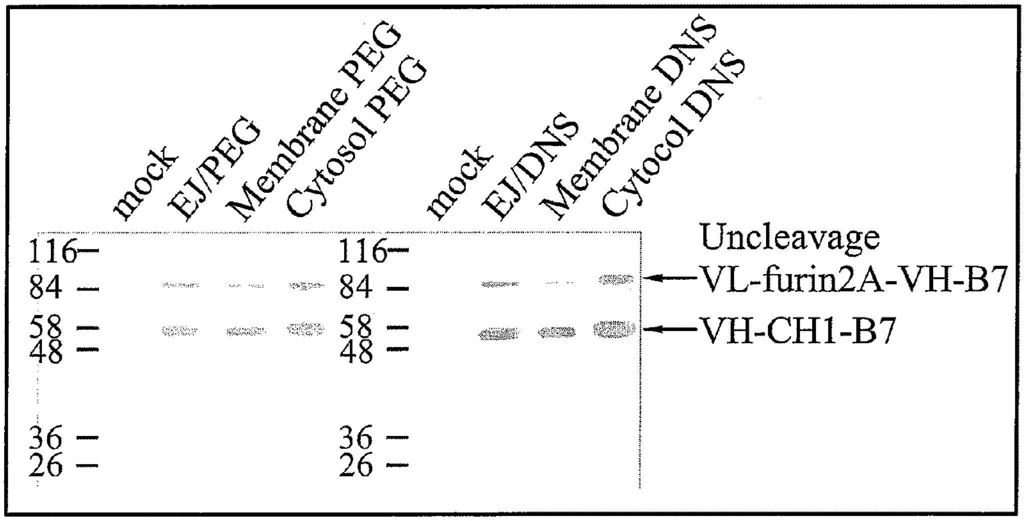
FIG. 4B shows the expression results and the molecular weights of the heavy chains after performing western blotting with anti-myc antigen monoclonal antibodies.

The vector (pLNCX) containing the recombinant nucleotide sequence encoding an anti-polyethylene glycol recombinant single chain membrane antibody (the sequence of SEQ ID No. 4) and the vector (pLNCX) containing the recombinant nucleotide sequence encoding an anti-dansyl recombinant single chain membrane antibody the sequence of (the sequence of SEQ ID No. 23) were transfected and expressed in Balb-3T3 cells, respectively. Western blotting was used to determine whether the light chains and the heavy chains of the two kinds of the antibodies mentioned above were separated during the translation. FIG. 4A shows the light chains detected by performing western blotting with anti-HA antigen monoclonal antibodies and FIG. 4B shows the heavy chains detected by performing western blotting with anti-myc antigen monoclonal antibodies. FIGS. 4A and 4B show that after the genes of the two kinds membrane antibodies were translated, the FMDV 2A processing sequence was cleaved to separate the light chain from the heavy chain and then the separated light chain and the heavy chain were assembled as a functional membrane antibody. Because the light chains of the two kinds of the antibodies in FIG. 4A show the correct molecular weights, respectively, the remaining 2A processing sequences after the light sequences had been completely cleaved by Furin protease in a Golgi apparatus, Moreover, by isolating the proteins of the cell membrane and the cytoplasm and performing a western blotting, it was confirmed that the single chain membrane antibodies expressed on the cell membranes were completely assembled functional membrane antibodies and not immature proteins with a non-cleaved 2A processing sequence.

Stability of the Single Chain Membrane Antibody In Vivo or In Vitro

Figure 5A:
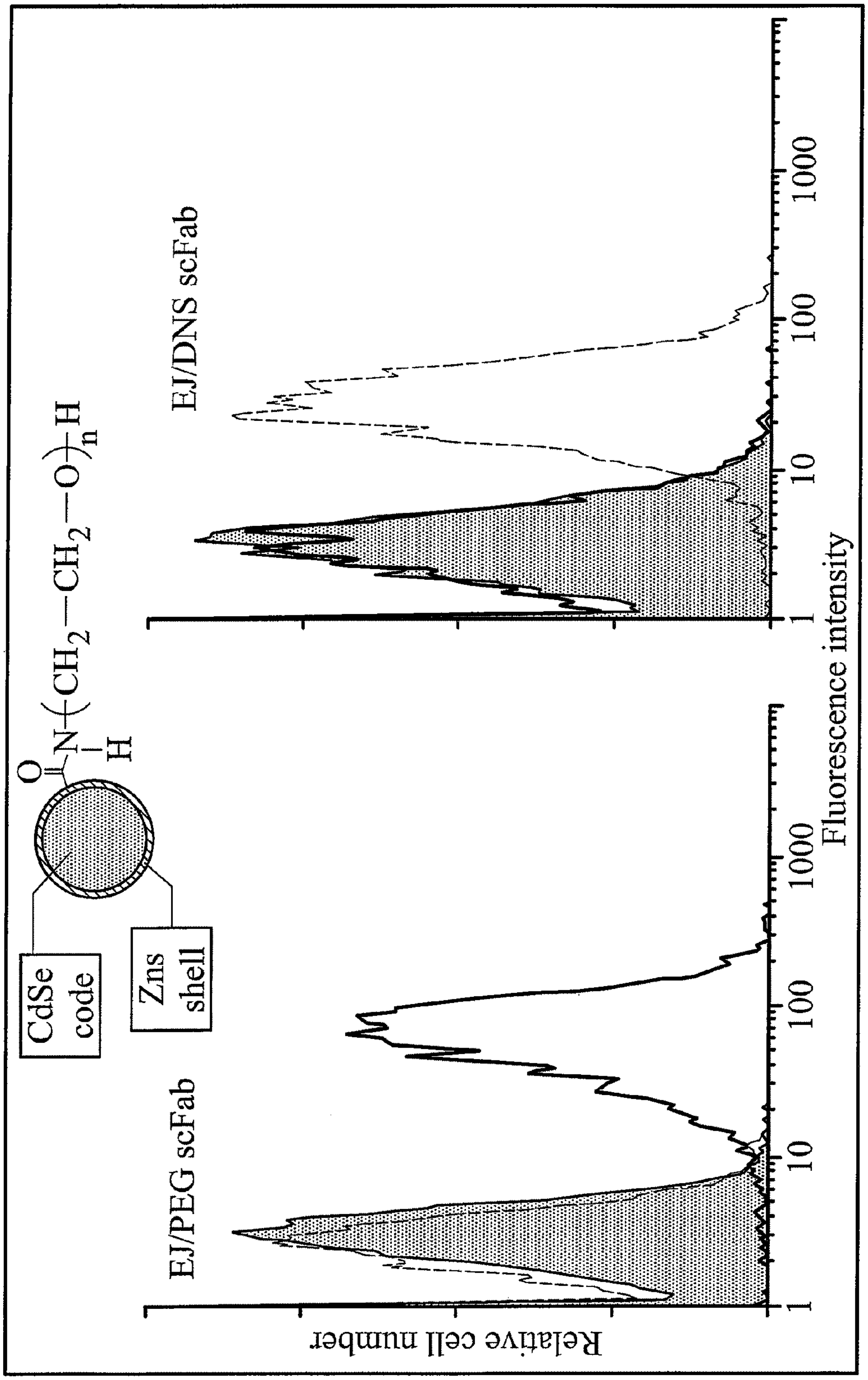
FIG. 5A shows the specificity testing results for in vitro binding between the PEG-Ouantum dots to anti-polyethylene glycol recombinant single chain membrane antibodies.
Figure 5B:
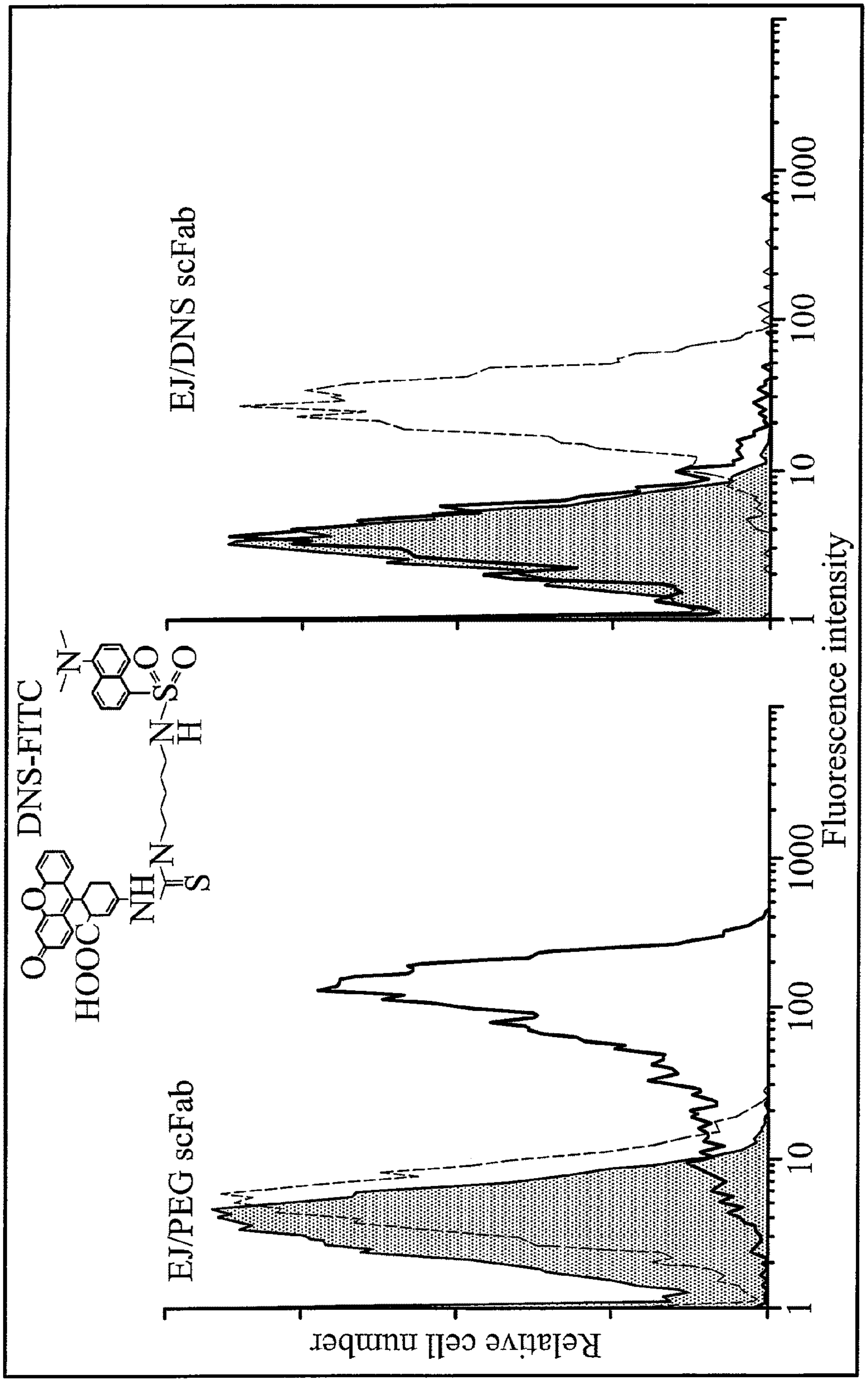
FIG. 5B shows the specificity testing results for in vivo binding between the PEG-Ouantum dots to anti-polyethylene glycol recombinant single chain membrane antibodies.

The vector (pLNCX) containing the recombinant nucleotide sequence encoding an anti-polyethylene glycol recombinant single chain membrane antibody (the sequence of SEQ ID No. 4) and the vector (pLNCX) containing the recombinant nucleotide sequence encoding an anti-anti-dansyl recombinant single chain membrane antibody (the sequence of SEQ ID No. 23) were transfected and expressed in EJ cells, respectively. Flow cytometry was used to analyze the ability for the polyethylene glycol-Ouantum dots (PEG-Ouantum dots) to bind to the cells expressing the anti-polyethylene glycol recombinant single chain membrane antibodies. The left part of FIG. 5A shows that in vitro, the PEG-Ouantum dot had the ability for specifically binding to the cells expressing the anti-polyethylene glycol recombinant single chain membrane antibodies (EJ/PEG scFab) and FIG. 5B shows that in vivo, the PEG-Ouantum dot also had the ability for specifically binding to the cells expressing the anti-polyethylene glycol recombinant single chain membrane antibodies (EJ/PEG scFab) isolated from the living being. As FIGS. 5A and 5B shows, the same mount of PEG-Ouantum dots was able to specifically bind to the cells expressing the anti-polyethylene glycol recombinant single chain membrane antibodies (EJ/PEG scFab) both in vitro and in vivo, confirming that the anti-polyethylene glycol recombinant single chain membrane antibodies are able to be expressed stably in vitro and in vivo. A similar result was also shown for cells expressing the anti-dansyl recombinant single chain membrane antibodies (the right parts of FIGS. 5A and 5B).

Figure 6A:
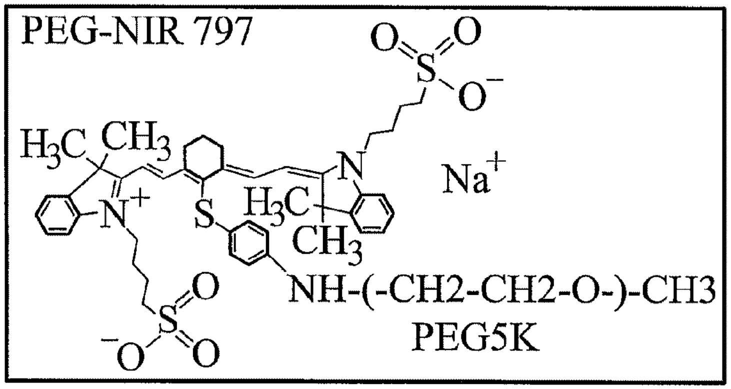
FIG. 6A shows the structure of a polyethylene glycol-fluorescent imaging agent ($PEG_{5000}$-NIR979)
Figure 6B:
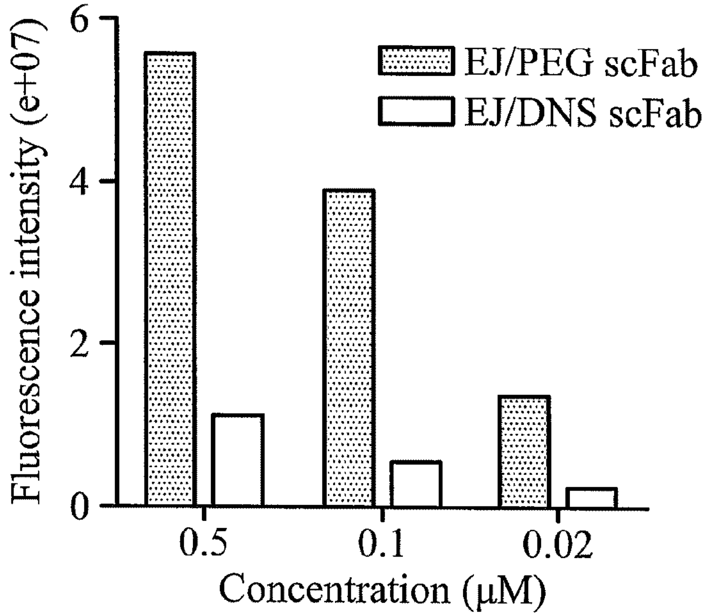
FIG. 6B shows the analyzed and digitized results of an IVIS imaging system for cells expressing the anti-polyethylene glycol recombinant single chain membrane antibodies or cells of a control group after reacting with different concentrations of PEG-fluorescent imaging agents.

Specificity for the Polyethylene Glycol-Fluorescent Imaging Agent (PEG-NIR979) In Vitro PEG-fluorescent imaging agents (PEG5000-NIR797) (FIG. 6A) with different concentration (0.5 μm, 0.1 μm and 0.02 μm) were used as probes to reacted with cells expressing the anti-polyethylene glycol recombinant single chain membrane antibodies (EJ/PEG scFab) and control group cells expressing the anti-dansyl recombinant single chain membrane antibodies (EJ/DNS scFab). Following an IVIS imaging system (Xenogen IVIS Imaging System 50 Series) was used to analyze the results and then the results were digitized. FIG. 6B shows that the PEG-fluorescent imaging agents were able to specifically bind to the cells expressing the anti-polyethylene glycol recombinant single chain membrane antibody (EJ/PEG scFab) and not the control group cells.

In Vitro Imaging by Polyethylene Glycol-Fluorescent Imaging Agent (PEG-NIR979)

Figure 7:
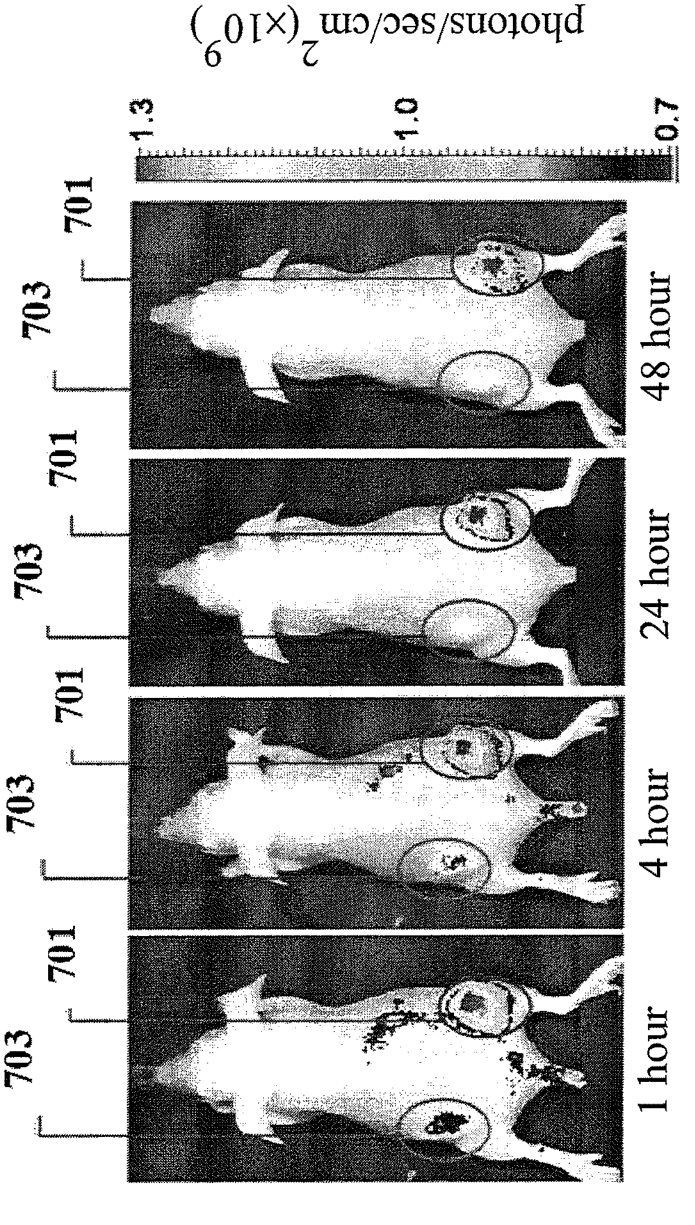
FIG. 7 shows the imaging results of an IVIS imaging system at different time points for tumor cells of expressing the anti-polyethylene glycol recombinant single chain membrane antibodies (EJ/PEG scFab) and tumor cells of a control group (EJ/DNS scFab) in a mouse after the mouse being injected with PEG-fluorescent imaging agents.

A PEG-fluorescent imaging agent ($PEG_{5000}$-NIR797) was injected into a mouse with tumors expressing the anti-polyethylene glycol recombinant single chain membrane antibody 701 (EJ/PEG scFab) and tumors of a control group expressing the anti-dansyl recombinant single chain membrane antibody 703 (EJ/DNS scFab) by intravenous injection. Following the mouse was imaged by an IVIS imaging system (Xenogen IVIS Imaging System 50 Series) at different times. The results were shown in FIG. 7. FIG. 7 shows that the PEG-fluorescent imaging agent was able to specifically bind to the tumors expressing the anti-polyethylene glycol recombinant single chain membrane antibody (EJ/PEG scFab) within 48 hours, and not to tumors of a control group.

Figure 8:
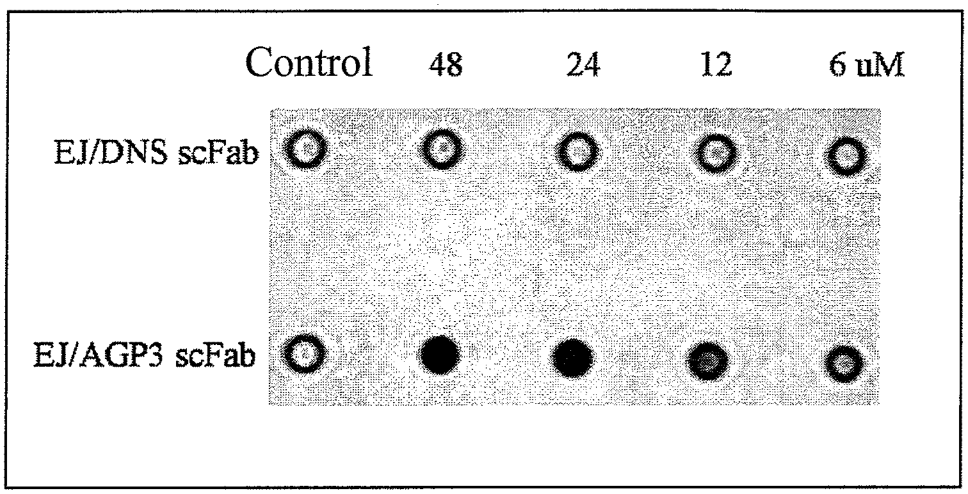
FIG. 8 shows imaging results of a magnetic resonance imaging system for cells expressing the anti-polyethylene glycol recombinant single chain membrane antibodies (EJ/PEG scFab) or cells of a control group (EJ/DNS scFab) after reacting with different concentrations of polyethylene glycol-iron oxide nanoparticles.

Specificity for the Polyethylene Glycol-Iron Oxide Nanoparticle Imaging Agent (PEG-NIR979) In Vitro FIG. 8 shows the imaging results for reacting PEG-$Fe_3O_4$ nanoparticles (T2 magnetic resonance imaging agent) with different concentrations with cells expressing the anti-polyethylene glycol recombinant single chain membrane antibodies (EJ/PEG scFab) and cells of a control group expressing the anti-dansyl recombinant single chain membrane antibodies (EJ/DNS scFab) by magnetic resonance imaging (MRI). As FIG. 8 shown, PEG-$Fe_3O_4$ nanoparticles with different concentrations (48, 24, 12 and 6) were able to specifically bind to the cells expressing the anti-polyethylene glycol recombinant single chain membrane antibodies (EJ/PEG scFab) (a dark signal represents the binding of the PEG-$Fe_3O_4$ nanoparticle to cells expressing the anti-polyethylene glycol recombinant single chain membrane antibodies), and not the control group cells.

In Vitro Imaging by Polyethylene Glycol-Iron Oxide Nanoparticle (PEG-$Fe_3O_4$ Nanoparticle)

Figure 9A:
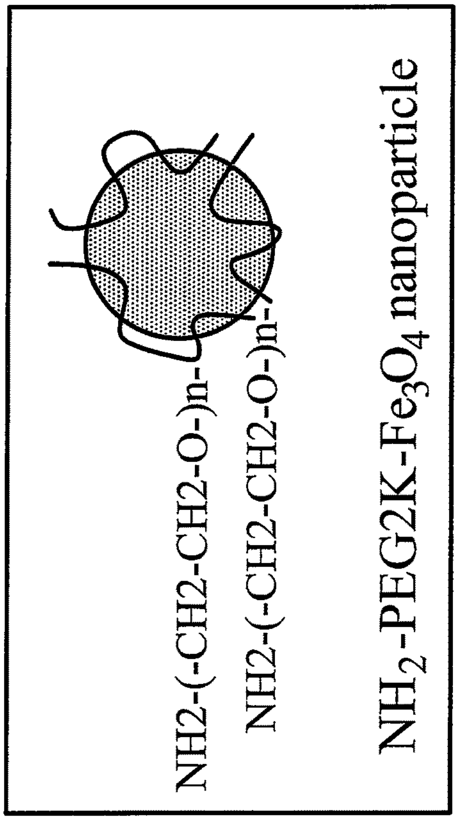
FIG. 9A shows the structure of a polyethylene glycol-iron oxide nanoparticle (PEG-$Fe_3O_4$)
Figure 9B:
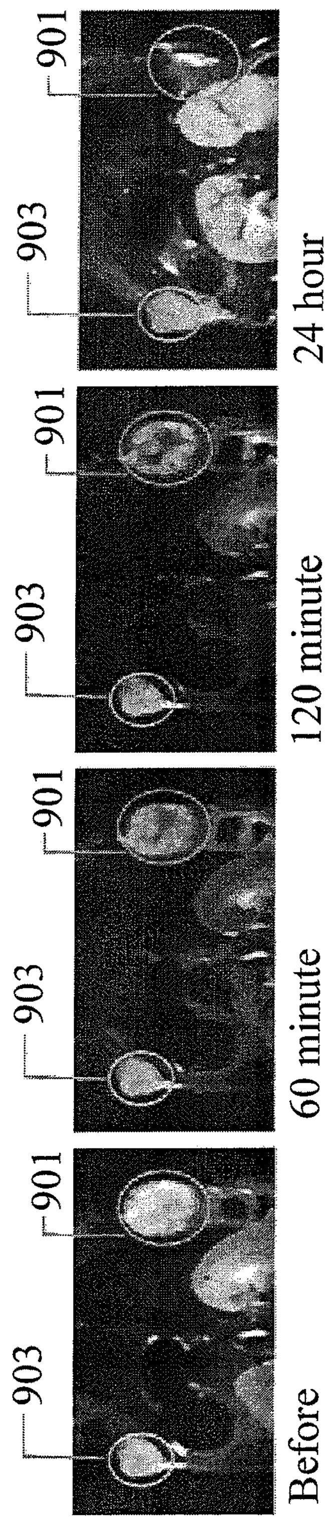
FIG. 9B shows the imaging results of an IVIS imaging system at different time points for tumor cells of a mouse expressing the anti-polyethylene glycol recombinant single chain membrane antibodies (EJ/PEG scFab) and tumor cells of a control group (EJ/DNS scFab) in a mouse after the mouse being injected with polyethylene glycol-iron oxide nanoparticles.

PEG-$Fe_3O_4$ nanoparticle (PEG5000-NIR797) (FIG. 9A) was injected into a mouse with tumors expressing the anti-polyethylene glycol recombinant single chain membrane antibody 901 (EJ/PEG scFab) and tumors of a control group expressing the anti-dansyl recombinant single chain membrane antibody 903 (EJ/DNS scFab) by intravenous injection. Following, the mouse was imaged by a T2 MRI imaging system at different times. The results are shown in FIG. 9B. FIG. 9B shows that the PEG-$Fe_3O_4$ nanoparticle was able to specifically bind to tumors expressing the anti-polyethylene glycol recombinant single chain membrane antibody (EJ/PEG scFab) (a dark signal represents the binding of the PEG-$Fe_3O_4$ nanoparticle to cells expressing the anti-polyethylene glycol recombinant single chain membrane antibodies), and not to tumors of a control group.

Specificity for the Polyethylene Glycol-$^{131}$Iodine In Vitro

Figure 10:
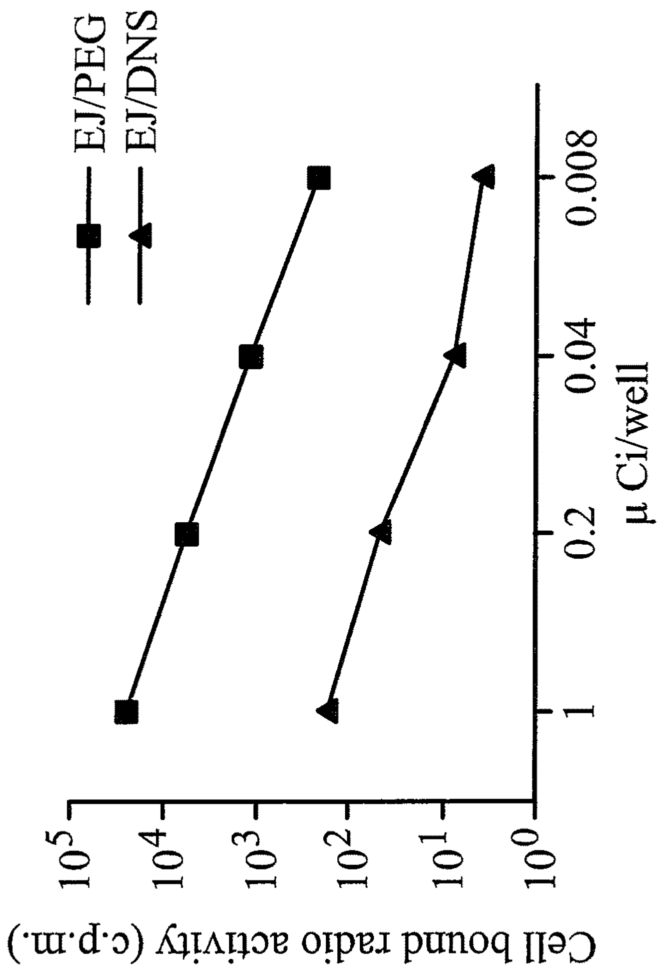
FIG. 10 shows the gamma counter detecting results for cells expressing the anti-polyethylene glycol recombinant single chain membrane antibodies (EJ/PEG scFab) or cells of a control group (EJ/DNS scFab) after reacting with different concentrations of polyethylene glycol-$^{131}$iodine.

FIG. 10 shows the gamma counter detecting results for cells expressing the anti-polyethylene glycol recombinant single chain membrane antibodies (EJ/PEG scFab) or cells of a control group expressing the anti-dansyl recombinant single chain membrane antibodies (EJ/DNS scFab) after reacting with different concentrations of polyethylene glycol-$^{131}$iodine. As FIG. 10 shows, polyethylene glycol-$^{131}$ iodine with different concentrations (1, 0.2, 0.04 and 0.08 μCi/50 μl/well) were able to specifically bind to the cells expressing the anti-polyethylene glycol recombinant single chain membrane antibodies (EJ/PEG scFab) (The radioactive intensity increased with increased concentrations), and not to the cells of the control group.

In Vitro Imaging by Polyethylene Glycol-$^{124}$ Iodine

Figure 11:
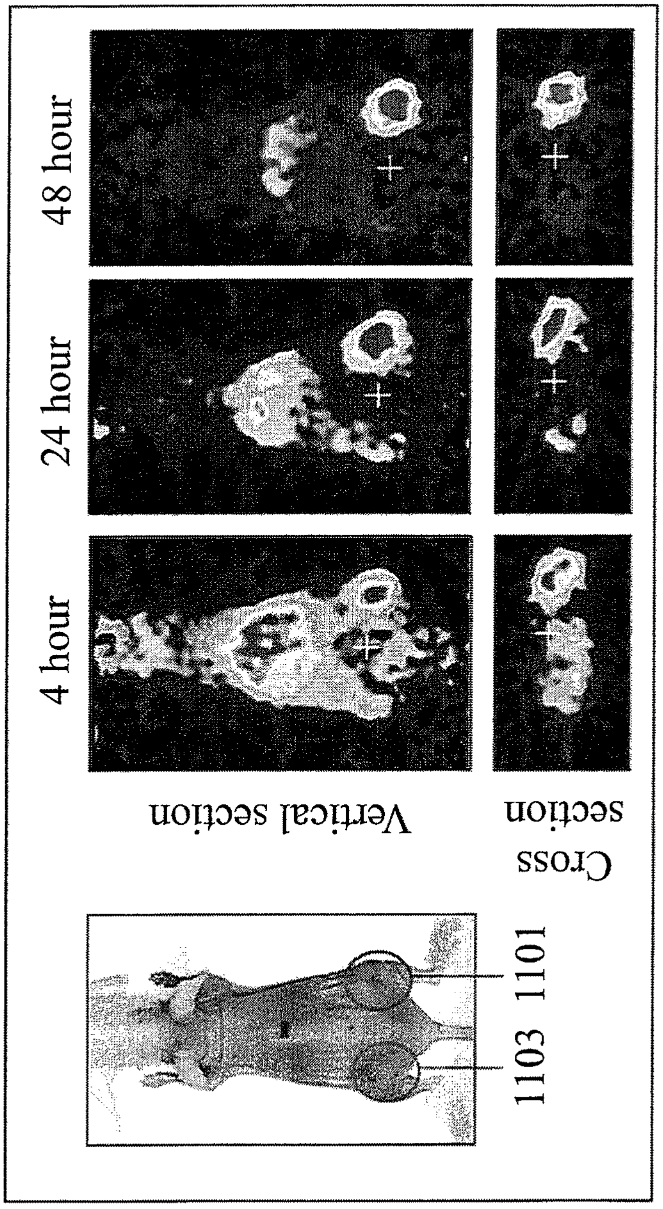
FIG. 11 shows the imaging results of a micro-PET imaging system at different time points for tumor cells of a mouse expressing the anti-polyethylene glycol recombinant single chain membrane antibodies (EJ/PEG scFab) and tumor cells of a control group (EJ/DNS scFab) in a mouse after the mouse being injected with polyethylene glycol-$^{124}$iodine.

Polyethylene glycol-$^{124}$ iodine was injected into a mouse with tumors expressing the anti-polyethylene glycol recombinant single chain membrane antibodies 1101 (EJ/PEG scFab) and tumors of a control group expressing the anti-dansyl recombinant single chain membrane antibodies 1103 (EJ/DNS scFab) by intravenous injection. Following, the mouse was imaged by a micro-PET imaging system at different times. The results are shown in FIG. 11. FIG. 11 shows that the polyethylene glycol-$^{124}$iodine was able to specifically bind to the tumors expressing the anti-polyethylene glycol recombinant single chain membrane antibodies (EJ/PEG scFab) (The radioactive intensity increased with increased concentrations), and not to tumors of a control group.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A recombinant nucleotide sequence, comprising the sequence of SEQ ID No. 1, SEQ ID No. 2, SEQ ID No. 3 or SEQ ID No. 4, wherein the recombinant nucleotide sequence encodes an anti-polyethylene glycol recombinant single chain membrane antibody.

2. The recombinant nucleotide sequence as claimed in claim 1, wherein the recombinant nucleotide sequence is a reporter gene.

3. The recombinant nucleotide sequence as claimed in claim 1, wherein the recombinant nucleotide sequence encodes an anti-polyethylene glycol recombinant single chain membrane antibody expressed on a cell membrane of a cell.

4. The recombinant nucleotide sequence as claimed in claim 3, wherein the cell comprises a stem cell, tumor cell or immune cell.

5. A vector comprising the recombinant nucleotide sequence as claimed in claim 1.

* * * * *

SEQUENCE LISTING

```
<160> NUMBER OF SEQ ID NOS: 25

<210> SEQ ID NO 1
<211> LENGTH: 1896
<212> TYPE: DNA
<213> ORGANISM: Artificial Sequence
<220> FEATURE:
<223> OTHER INFORMATION: Recombinant nucleotide sequence
      encoding an anti-polyethylene glycol recombinant single chain
      membrane antibody

<400> SEQUENCE: 1

gatattgtgt tgacgcaggc tgcattctcc aatccagtca ctcttggaac atcagcttcc     60

atctcctgca ggtctagtaa gagtctccta catagtaatg gcatcactta tttgtattgg    120

tatctgcaga agccaggcca gtctcctcag ctcctgattt atcagatgtc caaccttgcc    180

tcaggagtcc cagacaggtt cagtagcagt gggtcaggaa ctgatttcac actgagaatc    240

agcagagtgg aggctgagga tgtgggtgtt tattactgtg ctcaaaatct agaactattc    300

acgttcggct cggggacaaa gttggaaata aaacgggctg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgtcgagca    660

aaacgagcac cagtaaaaca aacactaaac ttcgacctac taaaactagc aggagacgta    720

gaatcaaacc caggaccaga agtgcagctg gtggagtctg ggggaggctt agtgaagcct    780

ggagggtccc tgaaactctc ctgtgcagcc tctggattca ctttcagtga ctattacatg    840

tattgggttc gccagactcc ggaaaagagg ctggagtggg tcgcaaccat tagtgatgat    900

ggtacttaca cctactatcc acacagtgtg aaggggcgat tcaccatctc cagagacagt    960

gccaagaaca acctgtacct gcaattgagc agtctgaagt ctgaggacac agccatgtat   1020

tactgtgcaa gaaatgatgc taggggggac tactggggtc aaggaacctc agtcaccgtc   1080

tcctcagaga gtcagtcctt cccaaatgtc ttcccccctcg tctcctgcga gagcccccctg   1140

tctgataaga atctggtggc catgggctgc ctggcccggg acttcctgcc cagcaccatt   1200

tccttcacct ggaactacca gaacaacact gaagtcatcc agggtatcag aaccttccca   1260

acactgagga cagggggcaa gtacctagcc acctcgcagg tgttgctgtc tcccaagagc   1320

atccttgaag gttcagatga atacctggta tgcgaaatcc actacggagg caaaaacaga   1380

gatctgcatg tgcccattcc agctgctgac ttctctaccc ccaacataac tgagtctgga   1440

aacccatctg cagacactaa aaggattacc tgctttgctt ccgggggttt cccaaagcct   1500
```

-continued

```
cgcttctctt ggttggaaaa tggaagagaa ttacctggca tcaatacgac aatttcccag   1560

gatcctgaat ctgaattgta caccattagt agccaactag atttcaatac gactcgcaac   1620

cacaccatta agtgtctcat taaatatgga gatgctcacg tgtcagagga cttcacctgg   1680

gaaaaacccc cagaagaccc tcctgatagc aagaacacac ttgtgctctt tggggcagga   1740

ttcggcgcag taataacagt cgtcgtcatc gttgtcatca tcaaatgctt ctgtaagcac   1800

agaagctgtt tcagaagaaa tgaggcaagc agagaaacaa acaacagcct taccttcggg   1860

cctgaagaag cattagctga acagaccgtc ttcctt                             1896


<210> SEQ ID NO 2
<211> LENGTH: 1923
<212> TYPE: DNA
<213> ORGANISM: Artificial Sequence
<220> FEATURE:
<223> OTHER INFORMATION: Recombinant nucleotide sequence
      encoding an anti-polyethylene glycol recombinant single chain
      membrane antibody

<400> SEQUENCE: 2

tatccatatg atgttccaga ttatgctgat attgtgttga cgcaggctgc attctccaat     60

ccagtcactc ttggaacatc agcttccatc tcctgcaggt ctagtaagag tctcctacat    120

agtaatggca tcacttattt gtattggtat ctgcagaagc caggccagtc tcctcagctc    180

ctgatttatc agatgtccaa ccttgcctca ggagtcccag acaggttcag tagcagtggg    240

tcaggaactg atttcacact gagaatcagc agagtggagg ctgaggatgt gggtgtttat    300

tactgtgctc aaaatctaga actattcacg ttcggctcgg ggacaaagtt ggaaataaaa    360

cgggctgatg ctgcaccaac tgtatccatc ttcccaccat ccagtgagca gttaacatct    420

ggaggtgcct cagtcgtgtg cttcttgaac aacttctacc ccaaagacat caatgtcaag    480

tggaagattg atggcagtga acgacaaaat ggcgtcctga acagttggac tgatcaggac    540

agcaaagaca gcacctacag catgagcagc accctcacgt tgaccaagga cgagtatgaa    600

cgacataaca gctatacctg tgaggccact cacaagacat caacttcacc cattgtcaag    660

agcttcaaca ggaatgagtg tcgagcaaaa cgagcaccag taaaacaaac actaaacttc    720

gacctactaa aactagcagg agacgtagaa tcaaacccag gaccagaagt gcagctggtg    780

gagtctgggg gaggcttagt gaagcctgga gggtccctga aactctcctg tgcagcctct    840

ggattcactt tcagtgacta ttacatgtat tgggttcgcc agactccgga aaagaggctg    900

gagtgggtcg caaccattag tgatgatggt acttacacct actatccaca cagtgtgaag    960

gggcgattca ccatctccag agacagtgcc aagaacaacc tgtacctgca attgagcagt   1020

ctgaagtctg aggacacagc catgtattac tgtgcaagaa atgatgctag gggggactac   1080

tggggtcaag gaacctcagt caccgtctcc tcagagagtc agtccttccc aaatgtcttc   1140

cccctcgtct cctgcgagag ccccctgtct gataagaatc tggtggccat gggctgcctg   1200

gcccgggact tcctgcccag caccatttcc ttcacctgga actaccagaa caacactgaa   1260

gtcatccagg gtatcagaac cttcccaaca ctgaggacag gggcaagta cctagccacc   1320

tcgcaggtgt tgctgtctcc caagagcatc cttgaaggtt cagatgaata cctggtatgc   1380

gaaatccact acggaggcaa aaacagagat ctgcatgtgc ccattccagc tgctgacttc   1440

tctacccccca acataactga gtctggaaac ccatctgcag acactaaaag gattacctgc   1500

tttgcttccg gggtttccc aaagcctcgc ttctcttggt tggaaaatgg aagagaatta   1560

cctggcatca atacgacaat ttcccaggat cctgaatctg aattgtacac cattagtagc   1620
```

```
caactagatt tcaatacgac tcgcaaccac accattaagt gtctcattaa atatggagat   1680

gctcacgtgt cagaggactt cacctgggaa aaaccccag aagaccctcc tgatagcaag    1740

aacacacttg tgctctttgg ggcaggattc ggcgcagtaa taacagtcgt cgtcatcgtt   1800

gtcatcatca aatgcttctg taagcacaga agctgtttca gaagaaatga ggcaagcaga   1860

gaaacaaaca acagccttac cttcgggcct gaagaagcat tagctgaaca gaccgtcttc   1920

ctt                                                                 1923
```

<210> SEQ ID NO 3
<211> LENGTH: 1926
<212> TYPE: DNA
<213> ORGANISM: Artificial Sequence
<220> FEATURE:
<223> OTHER INFORMATION: Recombinant nucleotide sequence encoding an anti-polyethylene glycol recombinant single chain membrane antibody

<400> SEQUENCE: 3

```
gatattgtgt tgacgcaggc tgcattctcc aatccagtca ctcttggaac atcagcttcc     60

atctcctgca ggtctagtaa gagtctccta catagtaatg gcatcactta tttgtattgg    120

tatctgcaga agccaggcca gtctcctcag ctcctgattt atcagatgtc caaccttgcc    180

tcaggagtcc cagacaggtt cagtagcagt gggtcaggaa ctgatttcac actgagaatc    240

agcagagtgg aggctgagga tgtgggtgtt tattactgtg ctcaaaatct agaactattc    300

acgttcggct cggggacaaa gttggaaata aaacgggctg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgtcgagca    660

aaacgagcac cagtaaaaca aacactaaac ttcgacctac taaaactagc aggagacgta    720

gaatcaaacc caggaccaga agtgcagctg gtggagtctg gggaggctt agtgaagcct     780

ggagggtccc tgaaactctc ctgtgcagcc tctggattca ctttcagtga ctattacatg    840

tattgggttc gccagactcc ggaaaagagg ctggagtggg tcgcaaccat tagtgatgat    900

ggtacttaca cctactatcc acacagtgtg aaggggcgat tcaccatctc cagagacagt    960

gccaagaaca acctgtacct gcaattgagc agtctgaagt ctgaggacac agccatgtat   1020

tactgtgcaa gaaatgatgc taggggggac tactggggtc aaggaacctc agtcaccgtc   1080

tcctcagaga gtcagtcctt cccaaatgtc ttccccctcg tctcctgcga gagccccctg   1140

tctgataaga atctggtggc catgggctgc ctggcccggg acttcctgcc cagcaccatt   1200

tccttcacct ggaactacca gaacaacact gaagtcatcc agggtatcag aaccttccca   1260

acactgagga cagggggcaa gtacctagcc acctcgcagg tgttgctgtc tcccaagagc   1320

atccttgaag gttcagatga atacctggta tgcgaaatcc actacggagg caaaaacaga   1380

gatctgcatg tgcccattcc agctgaacaa aaactcatct cagaagagga tctggctgac   1440

ttctctaccc ccaacataac tgagtctgga aacccatctg cagacactaa aaggattacc   1500

tgctttgctt ccgggggttt cccaaagcct cgcttctctt ggttggaaaa tggaagagaa   1560

ttacctggca tcaatacgac aatttcccag gatcctgaat ctgaattgta caccattagt   1620

agccaactag atttcaatac gactcgcaac cacaccatta agtgtctcat taaatatgga   1680
```

gatgctcacg tgtcagagga cttcacctgg gaaaaacccc cagaagaccc tcctgatagc 1740
aagaacacac ttgtgctctt tggggcagga ttcggcgcag taataacagt cgtcgtcatc 1800
gttgtcatca tcaaatgctt ctgtaagcac agaagctgtt tcagaagaaa tgaggcaagc 1860
agagaaacaa acaacagcct taccttcggg cctgaagaag cattagctga acagaccgtc 1920
ttcctt 1926

<210> SEQ ID NO 4
<211> LENGTH: 1953
<212> TYPE: DNA
<213> ORGANISM: Artificial Sequence
<220> FEATURE:
<223> OTHER INFORMATION: Recombinant nucleotide sequence encoding an anti-polyethylene glycol recombinant single chain membrane antibody

<400> SEQUENCE: 4
tatccatatg atgttccaga ttatgctgat attgtgttga cgcaggctgc attctccaat 60
ccagtcactc ttggaacatc agcttccatc tcctgcaggt ctagtaagag tctcctacat 120
agtaatggca tcacttattt gtattggtat ctgcagaagc caggccagtc tcctcagctc 180
ctgatttatc agatgtccaa ccttgcctca ggagtcccag acaggttcag tagcagtggg 240
tcaggaactg atttcacact gagaatcagc agagtggagg ctgaggatgt gggtgtttat 300
tactgtgctc aaaatctaga actattcacg ttcggctcgg ggacaaagtt ggaaataaaa 360
cgggctgatg ctgcaccaac tgtatccatc ttcccaccat ccagtgagca gttaacatct 420
ggaggtgcct cagtcgtgtg cttcttgaac aacttctacc ccaaagacat caatgtcaag 480
tggaagattg atggcagtga acgacaaaat ggcgtcctga acagttggac tgatcaggac 540
agcaaagaca gcacctacag catgagcagc accctcacgt tgaccaagga cgagtatgaa 600
cgacataaca gctatacctg tgaggccact cacaagacat caacttcacc cattgtcaag 660
agcttcaaca ggaatgagtg tcgagcaaaa cgagcaccag taaaacaaac actaaacttc 720
gacctactaa aactagcagg agacgtagaa tcaaacccag gaccagaagt gcagctggtg 780
gagtctgggg gaggcttagt gaagcctgga gggtccctga aactctcctg tgcagcctct 840
ggattcactt tcagtgacta ttacatgtat tgggttcgcc agactccgga aaagaggctg 900
gagtgggtcg caaccattag tgatgatggt acttacacct actatccaca cagtgtgaag 960
gggcgattca ccatctccag agacagtgcc aagaacaacc tgtacctgca attgagcagt 1020
ctgaagtctg aggacacagc catgtattac tgtgcaagaa atgatgctag gggggactac 1080
tggggtcaag gaacctcagt caccgtctcc tcagagagtc agtccttccc aaatgtcttc 1140
cccctcgtct cctgcgagag ccccctgtct gataagaatc tggtggccat gggctgcctg 1200
gcccgggact tcctgcccag caccatttcc ttcacctgga actaccagaa caacactgaa 1260
gtcatccagg gtatcagaac cttcccaaca ctgaggacag gggggcaagta cctagccacc 1320 tcgcaggtgt tgctgtctcc caagagcatc cttgaaggtt cagatgaata cctggtatgc 1380
gaaatccact acggaggcaa aaacagagat ctgcatgtgc ccattccagc tgaacaaaaa 1440
ctcatctcag aagaggatct ggctgacttc tctacccccca acataactga gtctggaaac 1500
ccatctgcag acactaaaag gattacctgc tttgcttccg ggggtttccc aaagcctcgc 1560
ttctcttggt tggaaaatgg aagagaatta cctggcatca atacgacaat ttcccaggat 1620
cctgaatctg aattgtacac cattagtagc caactagatt tcaatacgac tcgcaaccac 1680
accattaagt gtctcattaa atatggagat gctcacgtgt cagaggactt cacctgggaa 1740 aaaccccag aagaccctcc tgatagcaag aacacacttg tgctctttgg ggcaggattc 1800
ggcgcagtaa taacagtcgt cgtcatcgtt gtcatcatca aatgcttctg taagcacaga 1860
agctgtttca gaagaaatga ggcaagcaga gaaacaaaca acagccttac cttcgggcct 1920
gaagaagcat tagctgaaca gaccgtcttc ctt 1953

<210> SEQ ID NO 5
<211> LENGTH: 218
<212> TYPE: PRT
<213> ORGANISM: Mus musculus
<220> FEATURE:
<223> OTHER INFORMATION: Light chain sequence of
anti-polyethylene glycol recombinant single chain membrane
antibody

<400> SEQUENCE: 5

Asp Ile Val Leu Thr Gln Ala Ala Phe Ser Asn Pro Val Thr Leu Gly
1 5 10 15

Thr Ser Ala Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Leu Leu Ile Tyr Gln Met Ser Asn Leu Ala Ser Gly Val Pro
50 55 60

Asp Arg Phe Ser Ser Ser Gly Ser Gly Thr Asp Phe Thr Leu Arg Ile
65 70 75 80

Ser Arg Val Glu Ala Glu Asp Val Gly Val Tyr Tyr Cys Ala Gln Asn
85 90 95

Leu Glu Leu Phe Thr Phe Gly Ser Gly Thr Lys Leu Glu Ile Lys Arg
100 105 110

Ala Asp Ala Ala Pro Thr Val Ser Ile Phe Pro Pro Ser Ser Glu Gln
115 120 125

Leu Thr Ser Gly Gly Ala Ser Val Val Cys Phe Leu Asn Asn Phe Tyr
130 135 140

Pro Lys Asp Ile Asn Val Lys Trp Lys Ile Asp Gly Ser Glu Arg Gln
145 150 155 160

Asn Gly Val Leu Asn Ser Trp Thr Asp Gln Asp Ser Lys Asp Ser Thr
165 170 175

Tyr Ser Met Ser Ser Thr Leu Thr Leu Thr Lys Asp Glu Tyr Glu Arg
180 185 190

His Asn Ser Tyr Thr Cys Glu Ala Thr His Lys Thr Ser Thr Ser Pro
195 200 205

Ile Val Lys Ser Phe Asn Arg Asn Glu Cys
210 215

<210> SEQ ID NO 6
<211> LENGTH: 227
<212> TYPE: PRT
<213> ORGANISM: Artificial Sequence
<220> FEATURE:
<223> OTHER INFORMATION: Light chain sequence
of anti-polyethylene glycol recombinant single chain membrane
antibody

<400> SEQUENCE: 6

Tyr Pro Tyr Asp Val Pro Asp Tyr Ala Asp Ile Val Leu Thr Gln Ala
1 5 10 15

Ala Phe Ser Asn Pro Val Thr Leu Gly Thr Ser Ala Ser Ile Ser Cys
20 25 30

```
Arg Ser Ser Lys Ser Leu Leu His Ser Asn Gly Ile Thr Tyr Leu Tyr
        35                  40                  45

Trp Tyr Leu Gln Lys Pro Gly Gln Ser Pro Gln Leu Leu Ile Tyr Gln
    50                  55                  60

Met Ser Asn Leu Ala Ser Gly Val Pro Asp Arg Phe Ser Ser Ser Gly
65                  70                  75                  80

Ser Gly Thr Asp Phe Thr Leu Arg Ile Ser Arg Val Glu Ala Glu Asp
                85                  90                  95

Val Gly Val Tyr Tyr Cys Ala Gln Asn Leu Glu Leu Phe Thr Phe Gly
            100                 105                 110

Ser Gly Thr Lys Leu Glu Ile Lys Arg Ala Asp Ala Ala Pro Thr Val
        115                 120                 125

Ser Ile Phe Pro Pro Ser Ser Glu Gln Leu Thr Ser Gly Gly Ala Ser
    130                 135                 140

Val Val Cys Phe Leu Asn Asn Phe Tyr Pro Lys Asp Ile Asn Val Lys
145                 150                 155                 160

Trp Lys Ile Asp Gly Ser Glu Arg Gln Asn Gly Val Leu Asn Ser Trp
                165                 170                 175

Thr Asp Gln Asp Ser Lys Asp Ser Thr Tyr Ser Met Ser Ser Thr Leu
            180                 185                 190

Thr Leu Thr Lys Asp Glu Tyr Glu Arg His Asn Ser Tyr Thr Cys Glu
        195                 200                 205

Ala Thr His Lys Thr Ser Thr Ser Pro Ile Val Lys Ser Phe Asn Arg
    210                 215                 220

Asn Glu Cys
225
```

<210> SEQ ID NO 7
<211> LENGTH: 386
<212> TYPE: PRT
<213> ORGANISM: Artificial Sequence
<220> FEATURE:
<223> OTHER INFORMATION: Heavy chain and transmembrane region sequence of anti-polyethylene glycol recombinant single chain membrane antibody

<400> SEQUENCE: 7

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Asp Gly Thr Tyr Thr Tyr Tyr Pro His Ser Val
    50                  55                  60

Lys Gly Arg Phe Thr Ile Ser Arg Asp Ser Ala Lys Asn Asn Leu Tyr
65                  70                  75                  80

Leu Gln Leu Ser Ser Leu Lys Ser Glu Asp Thr Ala Met Tyr Tyr Cys
                85                  90                  95

Ala Arg Asn Asp Ala Arg Gly Asp Tyr Trp Gly Gln Gly Thr Ser Val
            100                 105                 110

Thr Val Ser Ser Glu Ser Gln Ser Phe Pro Asn Val Phe Pro Leu Val
        115                 120                 125

Ser Cys Glu Ser Pro Leu Ser Asp Lys Asn Leu Val Ala Met Gly Cys
    130                 135                 140

Leu Ala Arg Asp Phe Leu Pro Ser Thr Ile Ser Phe Thr Trp Asn Tyr
```

-continued

```
145                 150                 155                 160

Gln Asn Asn Thr Glu Val Ile Gln Gly Ile Arg Thr Phe Pro Thr Leu
                165                 170                 175

Arg Thr Gly Gly Lys Tyr Leu Ala Thr Ser Gln Val Leu Leu Ser Pro
            180                 185                 190

Lys Ser Ile Leu Glu Gly Ser Asp Glu Tyr Leu Val Cys Glu Ile His
        195                 200                 205

Tyr Gly Gly Lys Asn Arg Asp Leu His Val Pro Ile Pro Ala Ala Asp
    210                 215                 220

Phe Ser Thr Pro Asn Ile Thr Glu Ser Gly Asn Pro Ser Ala Asp Thr
225                 230                 235                 240

Lys Arg Ile Thr Cys Phe Ala Ser Gly Gly Phe Pro Lys Pro Arg Phe
                245                 250                 255

Ser Trp Leu Glu Asn Gly Arg Glu Leu Pro Gly Ile Asn Thr Thr Ile
            260                 265                 270

Ser Gln Asp Pro Glu Ser Glu Leu Tyr Thr Ile Ser Ser Gln Leu Asp
        275                 280                 285

Phe Asn Thr Thr Arg Asn His Thr Ile Lys Cys Leu Ile Lys Tyr Gly
    290                 295                 300

Asp Ala His Val Ser Glu Asp Phe Thr Trp Glu Lys Pro Pro Glu Asp
305                 310                 315                 320

Pro Pro Asp Ser Lys Asn Thr Leu Val Leu Phe Gly Ala Gly Phe Gly
                325                 330                 335

Ala Val Ile Thr Val Val Val Ile Val Val Ile Ile Lys Cys Phe Cys
            340                 345                 350

Lys His Arg Ser Cys Phe Arg Arg Asn Glu Ala Ser Arg Glu Thr Asn
        355                 360                 365

Asn Ser Leu Thr Phe Gly Pro Glu Glu Ala Leu Ala Glu Gln Thr Val
    370                 375                 380

Phe Leu
385


<210> SEQ ID NO 8
<211> LENGTH: 396
<212> TYPE: PRT
<213> ORGANISM: Artificial Sequence
<220> FEATURE:
<223> OTHER INFORMATION: Heavy chain and transmembrane region sequence
      of anti-polyethylene glycol recombinant single chain membrane
      antibody

<400> SEQUENCE: 8

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Asp Gly Thr Tyr Thr Tyr Tyr Pro His Ser Val
    50                  55                  60

Lys Gly Arg Phe Thr Ile Ser Arg Asp Ser Ala Lys Asn Asn Leu Tyr
65                  70                  75                  80

Leu Gln Leu Ser Ser Leu Lys Ser Glu Asp Thr Ala Met Tyr Tyr Cys
                85                  90                  95

Ala Arg Asn Asp Ala Arg Gly Asp Tyr Trp Gly Gln Gly Thr Ser Val
            100                 105                 110
```

-continued

```
Thr Val Ser Ser Glu Ser Gln Ser Phe Pro Asn Val Phe Pro Leu Val
        115                 120                 125

Ser Cys Glu Ser Pro Leu Ser Asp Lys Asn Leu Val Ala Met Gly Cys
    130                 135                 140

Leu Ala Arg Asp Phe Leu Pro Ser Thr Ile Ser Phe Thr Trp Asn Tyr
145                 150                 155                 160

Gln Asn Asn Thr Glu Val Ile Gln Gly Ile Arg Thr Phe Pro Thr Leu
                165                 170                 175

Arg Thr Gly Gly Lys Tyr Leu Ala Thr Ser Gln Val Leu Leu Ser Pro
            180                 185                 190

Lys Ser Ile Leu Glu Gly Ser Asp Glu Tyr Leu Val Cys Glu Ile His
        195                 200                 205

Tyr Gly Gly Lys Asn Arg Asp Leu His Val Pro Ile Pro Ala Glu Gln
    210                 215                 220

Lys Leu Ile Ser Glu Glu Asp Leu Ala Asp Phe Ser Thr Pro Asn Ile
225                 230                 235                 240

Thr Glu Ser Gly Asn Pro Ser Ala Asp Thr Lys Arg Ile Thr Cys Phe
                245                 250                 255

Ala Ser Gly Gly Phe Pro Lys Pro Arg Phe Ser Trp Leu Glu Asn Gly
            260                 265                 270

Arg Glu Leu Pro Gly Ile Asn Thr Thr Ile Ser Gln Asp Pro Glu Ser
        275                 280                 285

Glu Leu Tyr Thr Ile Ser Ser Gln Leu Asp Phe Asn Thr Thr Arg Asn
    290                 295                 300

His Thr Ile Lys Cys Leu Ile Lys Tyr Gly Asp Ala His Val Ser Glu
305                 310                 315                 320

Asp Phe Thr Trp Glu Lys Pro Pro Glu Asp Pro Pro Asp Ser Lys Asn
                325                 330                 335

Thr Leu Val Leu Phe Gly Ala Gly Phe Gly Ala Val Ile Thr Val Val
            340                 345                 350

Val Ile Val Val Ile Ile Lys Cys Phe Cys Lys His Arg Ser Cys Phe
        355                 360                 365

Arg Arg Asn Glu Ala Ser Arg Glu Thr Asn Asn Ser Leu Thr Phe Gly
    370                 375                 380

Pro Glu Glu Ala Leu Ala Glu Gln Thr Val Phe Leu
385                 390                 395


<210> SEQ ID NO 9
<211> LENGTH: 654
<212> TYPE: DNA
<213> ORGANISM: Mus musculus
<220> FEATURE:
<223> OTHER INFORMATION: Gene sequence of a variable light chain - kappa
      constant (VL-CM) region of the hybridoma secreting
      anti-polyethylene glycol monoclonal antibody

<400> SEQUENCE: 9

gatattgtgt tgacgcaggc tgcattctcc aatccagtca ctcttggaac atcagcttcc     60

atctcctgca ggtctagtaa gagtctccta catagtaatg gcatcactta tttgtattgg    120

tatctgcaga agccaggcca gtctcctcag ctcctgattt atcagatgtc caaccttgcc    180

tcaggagtcc cagacaggtt cagtagcagt gggtcaggaa ctgatttcac actgagaatc    240

agcagagtgg aggctgagga tgtgggtgtt tattactgtg ctcaaaatct agaactattc    300

acgttcggct cggggacaaa gttggaaata aaacgggctg atgctgcacc aactgtatcc    360

atcttcccac catccagtga gcagttaaca tctggaggtg cctcagtcgt gtgcttcttg    420
```

-continued

```
aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgt          654


<210> SEQ ID NO 10
<211> LENGTH: 12
<212> TYPE: DNA
<213> ORGANISM: Artificial Sequence
<220> FEATURE:
<223> OTHER INFORMATION: Furin-cleavage site

<400> SEQUENCE: 10

cgagcaaaac ga                                                          12


<210> SEQ ID NO 11
<211> LENGTH: 72
<212> TYPE: DNA
<213> ORGANISM: Aphtae epizooticae
<220> FEATURE:
<223> OTHER INFORMATION: 2A self-processing sequence

<400> SEQUENCE: 11

gcaccagtaa aacaaacact aaacttcgac ctactaaaac tagcaggaga cgtagaatca     60

aacccaggac ca                                                          72


<210> SEQ ID NO 12
<211> LENGTH: 666
<212> TYPE: DNA
<213> ORGANISM: Mus musculus
<220> FEATURE:
<223> OTHER INFORMATION: Gene sequence of a variable heavy chain - heavy
      chain first constant (VH-CH1) region of the hybridoma secreting
      anti-polyethylene glycol monoclonal antibody

<400> SEQUENCE: 12

gaagtgcagc tggtggagtc tgggggaggc ttagtgaagc ctggagggtc cctgaaactc     60

tcctgtgcag cctctggatt cactttcagt gactattaca tgtattgggt tcgccagact    120

ccggaaaaga ggctggagtg ggtcgcaacc attagtgatg atggtactta cacctactat    180

ccacacagtg tgaaggggcg attcaccatc tccagagaca gtgccaagaa caacctgtac    240

ctgcaattga gcagtctgaa gtctgaggac acagccatgt attactgtgc aagaaatgat    300

gctagggggg actactgggg tcaaggaacc tcagtcaccg tctcctcaga gagtcagtcc    360

ttcccaaatg tcttcccct cgtctcctgc gagagccccc tgtctgataa gaatctggtg    420

gccatgggct gcctggcccg ggacttcctg cccagcacca tttccttcac ctggaactac    480

cagaacaaca ctgaagtcat ccagggtatc agaaccttcc caacactgag gacagggggc    540

aagtacctag ccacctcgca ggtgttgctg tctcccaaga gcatccttga aggttcagat    600

gaatacctgg tatgcgaaat ccactacgga ggcaaaaaca gagatctgca tgtgcccatt    660

ccagct                                                                666


<210> SEQ ID NO 13
<211> LENGTH: 1404
<212> TYPE: DNA
<213> ORGANISM: Artificial Sequence
<220> FEATURE:
<223> OTHER INFORMATION: Sequence containing SEQ ID. Nos. 9-12

<400> SEQUENCE: 13
```

-continued

```
gatattgtgt tgacgcaggc tgcattctcc aatccagtca ctcttggaac atcagcttcc     60

atctcctgca ggtctagtaa gagtctccta catagtaatg gcatcactta tttgtattgg    120

tatctgcaga agccaggcca gtctcctcag ctcctgattt atcagatgtc caaccttgcc    180

tcaggagtcc cagacaggtt cagtagcagt gggtcaggaa ctgatttcac actgagaatc    240

agcagagtgg aggctgagga tgtgggtgtt tattactgtg ctcaaaatct agaactattc    300

acgttcggct cggggacaaa gttggaaata aaacgggctg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgtcgagca    660

aaacgagcac cagtaaaaca aacactaaac ttcgacctac taaaactagc aggagacgta    720

gaatcaaacc caggaccaga agtgcagctg gtggagtctg gggaggctt agtgaagcct    780

ggagggtccc tgaaactctc ctgtgcagcc tctggattca ctttcagtga ctattacatg    840

tattgggttc gccagactcc ggaaaagagg ctggagtggg tcgcaaccat tagtgatgat    900

ggtacttaca cctactatcc acacagtgtg aaggggcgat tcaccatctc cagagacagt    960

gccaagaaca acctgtacct gcaattgagc agtctgaagt ctgaggacac agccatgtat   1020

tactgtgcaa gaaatgatgc tagggggac tactggggtc aaggaacctc agtcaccgtc   1080

tcctcagaga gtcagtcctt cccaaatgtc ttcccccctcg tctcctgcga gagcccccctg   1140

tctgataaga atctggtggc catgggctgc ctggcccggg acttcctgcc cagcaccatt   1200

tccttcacct ggaactacca gaacaacact gaagtcatcc agggtatcag aaccttccca   1260

acactgagga caggggggcaa gtacctagcc acctcgcagg tgttgctgtc tcccaagagc   1320

atccttgaag gttcagatga atacctggta tgcgaaatcc actacggagg caaaaacaga   1380

gatctgcatg tgcccattcc agct                                          1404
```

```
<210> SEQ ID NO 14
<211> LENGTH: 492
<212> TYPE: DNA
<213> ORGANISM: Mus musculus
<220> FEATURE:
<223> OTHER INFORMATION: Nucleotide sequence encoding a transmembrane
      region of B7 protein

<400> SEQUENCE: 14

gctgacttct ctacccccaa cataactgag tctggaaacc catctgcaga cactaaaagg     60

attacctgct ttgcttccgg gggtttccca aagcctcgct tctcttggtt ggaaaatgga    120

agagaattac ctggcatcaa tacgacaatt tcccaggatc ctgaatctga attgtacacc    180

attagtagcc aactagattt caatacgact cgcaaccaca ccattaagtg tctcattaaa    240

tatggagatg ctcacgtgtc agaggacttc acctgggaaa aacccccaga agaccctcct    300

gatagcaaga acacacttgt gctctttggg gcaggattcg gcgcagtaat aacagtcgtc    360

gtcatcgttg tcatcatcaa atgcttctgt aagcacagaa gctgtttcag aagaaatgag    420

gcaagcagag aaacaaacaa cagccttacc ttcgggcctg aagaagcatt agctgaacag    480

accgtcttcc tt                                                         492

<210> SEQ ID NO 15
<211> LENGTH: 27
```

<212> TYPE: DNA
<213> ORGANISM: Influenza virus
<220> FEATURE:
<223> OTHER INFORMATION: Nucleotide sequence encoding hemagglutinin (HA)

<400> SEQUENCE: 15
tatccatatg atgttccaga ttatgct 27

<210> SEQ ID NO 16
<211> LENGTH: 30
<212> TYPE: DNA
<213> ORGANISM: Homo sapiens
<220> FEATURE:
<223> OTHER INFORMATION: Nucleotide sequence encoding myc protein

<400> SEQUENCE: 16
gaacaaaaac tcatctcaga agaggatctg 30

<210> SEQ ID NO 17
<211> LENGTH: 32
<212> TYPE: DNA
<213> ORGANISM: Artificial Sequence
<220> FEATURE:
<223> OTHER INFORMATION: Forward primer

<400> SEQUENCE: 17
gggagctcga yattgtgmts acmcarwctm ca 32

<210> SEQ ID NO 18
<211> LENGTH: 18
<212> TYPE: DNA
<213> ORGANISM: Artificial Sequence
<220> FEATURE:
<223> OTHER INFORMATION: Reverse primer

<400> SEQUENCE: 18
acactcattc ctgttgaa 18

<210> SEQ ID NO 19
<211> LENGTH: 29
<212> TYPE: DNA
<213> ORGANISM: Artificial Sequence
<220> FEATURE:
<221> NAME/KEY: modified_base
<222> LOCATION: 15
<223> OTHER INFORMATION: Forward primer, n=a or g or c or t/u

<400> SEQUENCE: 19
ccggaattcs argtnmagct gsagsagtc 29

<210> SEQ ID NO 20
<211> LENGTH: 18
<212> TYPE: DNA
<213> ORGANISM: Artificial Sequence
<220> FEATURE:
<223> OTHER INFORMATION: Reverse primer

<400> SEQUENCE: 20
agctggaatg ggcacatg 18

<210> SEQ ID NO 21
<211> LENGTH: 31
<212> TYPE: DNA
<213> ORGANISM: Artificial Sequence
<220> FEATURE:
<223> OTHER INFORMATION: Forward primer

<400> SEQUENCE: 21

-continued ggcccagccg gccgatattg tgttgacgca g 31

<210> SEQ ID NO 22
<211> LENGTH: 45
<212> TYPE: DNA
<213> ORGANISM: Artificial Sequence
<220> FEATURE:
<223> OTHER INFORMATION: Reverse primer

<400> SEQUENCE: 22
ttgttttact ggtgctcgtt ttgctcgaca ctcattcctg ttgaa 45

<210> SEQ ID NO 23
<211> LENGTH: 90
<212> TYPE: DNA
<213> ORGANISM: Artificial Sequence
<220> FEATURE:
<223> OTHER INFORMATION: Forward primer

<400> SEQUENCE: 23
gcaccagtaa aacaaacact aaacttcgac ctactaaaac tagcaggaga cgtagaatca 60
aacccaggac cagaagtgca gctggtggag 90

<210> SEQ ID NO 24
<211> LENGTH: 24
<212> TYPE: DNA
<213> ORGANISM: Artificial Sequence
<220> FEATURE:
<223> OTHER INFORMATION: Reverse primer

<400> SEQUENCE: 24
gtcgacagct ggaatgggca catg 24

<210> SEQ ID NO 25
<211> LENGTH: 1974
<212> TYPE: DNA
<213> ORGANISM: Artificial Sequence
<220> FEATURE:
<223> OTHER INFORMATION: Recombinant nucleotide sequence
encoding an anti-dansyl recombinant single chain membrane antibody

<400> SEQUENCE: 25
tatccatatg atgttccaga ttatgctgat gttgtgatga cccaaactcc actctccctg 60
cctgtcagtc ttggaaatca agcctccatc tcttgcagat ctagtcagag ccttgtacac 120
agtaatggaa acacctattt acattggtac ctgcagaagc caggccagtc tccaaagctc 180
ctgatctaca aagtttccaa ccgattttct ggggtcccag acaggttcag tggcagtgga 240
tcagggacag atttcacact caagatcagc agagtggagg ctgaggatct gggagtttat 300
ttctgctctc aaagtacaca tgttccattc acgttcggct cggggacaaa gttggaaata 360
aaacgtgctg atgctgcacc aactgtatcc atcttcccac catccagtga gcagttaaca 420
tctggaggtg cctcagtcgt gtgcttcttg aacaacttct accccaaaga catcaatgtc 480
aagtggaaga ttgatggcag tgaacgacaa aatggcgtcc tgaacagttg gactgatcag 540
gacagcaaag acagcaccta cagcatgagc agcaccctca cgttgaccaa ggacgagtat 600
gaacgacata acagctatac ctgtgaggcc actcacaaga catcaacttc acccattgtc 660
aagagcttca acaggaatga gtgtcgagca aaacgagcac cagtaaaaca aacactaaac 720
ttcgacctac taaaactagc aggagacgta gaatcaaacc caggaccaag tgaagtgaag 780
cttgaggagt ctggaggagg cttggtgcaa cctggaggat ccatgaaact ctcttgtgct 840

-continued

```
acttctggat tcacttttag tgatgcctgg atggactggg tccgccagtc tccagagaag    900
gggcttgagt gggttgctga aattagaaac aaagctaata atcatgcaac atactatgct    960
gagtctgtga aagggaggtt caccatctca agagatgatt ccaaaaggag agtgtacctg   1020
caaatgaaca ccttaagagc tgaagacact ggcatttatt actgtaccgg gatctactat   1080
cattacccct ggtttgctta ctggggccaa gggactctgg tcactgtctc tgcagagagt   1140
cagtccttcc caaatgtctt cccccctcgtc tcctgcgaga gcccccctgtc tgataagaat  1200
ctggtggcca tgggctgcct ggcccgggac ttcctgccca gcaccatttc cttcacctgg   1260
aactaccaga acaacactga agtcatccag ggtatcagaa ccttcccaac actgaggaca   1320
gggggcaagt acctagccac ctcgcaggtg ttgctgtctc ccaagagcat ccttgaaggt   1380
tcagatgaat acctggtatg cgaaatccac tacggaggca aaaacagaga tctgcatgtg   1440
cccattccag ctgaacaaaa actcatctca gaagaggatc tggctgactt ctctaccccc   1500
aacataactg agtctggaaa cccatctgca gacactaaaa ggattacctg ctttgcttcc   1560
gggggtttcc caaagcctcg cttctcttgg ttggaaaatg gaagagaatt acctggcatc   1620
aatacgacaa tttcccagga tcctgaatct gaattgtaca ccattagtag ccaactagat   1680
ttcaatacga ctcgcaacca caccattaag tgtctcatta aatatggaga tgctcacgtg   1740
tcagaggact tcacctggga aaaaccccca gaagaccctc ctgatagcaa gaacacactt   1800
gtgctctttg gggcaggatt cggcgcagta ataacagtcg tcgtcatcgt tgtcatcatc   1860
aaatgcttct gtaagcacag aagctgtttc agaagaaatg aggcaagcag agaaacaaac   1920
aacagcctta ccttcgggcc tgaagaagca ttagctgaac agaccgtctt cctt         1974
```